United States Patent [19]

Carlock

[11] 4,198,353

[45] Apr. 15, 1980

[54] IRIDIUM OR RHODIUM TRIHALIDE POLYMER BOUND HYDROGENATION AND HYDROFORMYLATION CATALYST

[75] Inventor: John T. Carlock, Ponca City, Okla.

[73] Assignee: Conoco, Inc., Ponca City, Okla.

[21] Appl. No.: 973,288

[22] Filed: Dec. 26, 1978

Related U.S. Application Data

[63] Continuation-in-part of Ser. No. 924,596, Jul. 14, 1978.

[51] Int. Cl.$^2$ .............................................. C07C 45/10
[52] U.S. Cl. ............................ 260/604 HF; 568/909; 252/431 N
[58] Field of Search ................. 260/604 HF; 568/909; 252/438, 431 N

[56] References Cited

U.S. PATENT DOCUMENTS

| | | | |
|---|---|---|---|
| 3,499,932 | 3/1970 | Pruett et al. | 260/604 HF |
| 3,527,809 | 8/1970 | Pruett et al. | 260/604 HF |
| 3,636,159 | 1/1972 | Solomon | 260/604 HF |
| 3,652,676 | 3/1972 | Kahale et al. | 260/604 HF |
| 3,821,311 | 6/1974 | Hughes et al. | 260/604 HF |
| 3,825,601 | 7/1974 | Rennick | 260/604 HF |
| 3,907,847 | 8/1975 | Keblys | 260/604 HF |
| 3,948,999 | 4/1976 | Homeier | 260/604 HF |

OTHER PUBLICATIONS

Tetrahedron Letters, (1971), pp. 4787-4790, (50), Grubbs et al.
Jour. Macrmol. Sci. Chem., (1972), 13, (12), pp. 828-832.
Advanced Chem. Series, 132, p. 240, (1974), Jurewicz et al.
Tokyo Kogyo Shikensho Hokoku, V 67, p. 340, (1972), Ogata et al.
Jour. Chem. Society, (1971), p. 804, Abley et al.
Chem. Ing. Tech., V. 44, p. 708, (1972), Fell et al.

*Primary Examiner*—Werren B. Lone
*Attorney, Agent, or Firm*—Cortlan R. Schupbach, Jr.

[57] ABSTRACT

A catalyst of the general structure $\text{\textcircled{P}}-\text{MCl}_3$ wherein M is rhodium or iridium and $\text{\textcircled{P}}$ is a heterocyclic nitrogen-containing polymer has been found to be an effective heterogeneous hydroformylation catalyst at temperatures of from about 60° to about 150° C. and $H_2/CO$ gas pressures of from about 300 to about 3500 psig for most primary and internal olefins, producing an increased amount of linear normal aldehydes. When the reactor gas is altered to hydrogen, the catalyst further converts aldehydes formed by hydroformylation to alcohols under the same reaction conditions. The catalyst is oxygen stable, heterogeneous, and easily recovered.

2 Claims, No Drawings

IRIDIUM OR RHODIUM TRIHALIDE POLYMER BOUND HYDROGENATION AND HYDROFORMYLATION CATALYST

This application is a continuation-in-part of Ser. No. 924,596, filed July 14, 1978.

The instant invention relates to airstable heterogeneous rhodium and iridium trihalide catalysts which are polymer bound. More particularly, the instant invention relates to airstable heterogeneous rhodium and iridium trihalide polymer bound catalyst which allow hydroformylation to occur under reactor conditions where carbon monoxide and hydrogen are present and allow hydrogenation to occur under essentially pure hydrogen for many unsaturated organic compounds.

The hydroformylation of terminal (or alpha) olefins by certain homogeneous rhodium catalysts is known in the art. Representative examples of references describing rhodium catalysts used in hydroformylation reactions and reaction conditions necessary are found in U.S. Pat. Nos. 3,917,661; 3,907,847; 3,821,311; 3,499,932; 3,527,809; 3,825,601; 3,948,999; and 3,984,478. Literature references of polymer-bound catalysts include *Tetrahedron Letters*, 1971 (50) 4787–90, Grubbs et al, *Journal of Macrmol. Sci. Chem.*, 1972, 13 (12), 828–32. While these references are not exhaustive of the art, they appear to be representative of hydroformylation in the current state of the art. However, these catalysts and reactions are generally very poor when used with internal olefins when the catalysts are dissolved in the reaction mixture, said catalysts being difficult to recover. In addition, these materials usually employ Group V ligands such as phosphines, phosphites, organo-arsines, and organo-antimony compounds which are very toxic and are air sensitive. Recovery of the catalyst is important since rhodium and iridium are an extremely expensive metal and the product cost rises sharply with each percentage drop in rhodium or iridium recovery from a previous reaction.

Hydroformylation is a reaction which converts olefins to aldehydes such as shown in the formula below:

RC=CR→R—CH—CR—CHO, wherein R is hydrogen or an alkyl. Usually the hydroformylation procedure is followed by the hydrogenation of aldehydes to produce alcohol. However, the hydrogenation procedure is relatively simple and can be carried out by any one of several well-known means. In this procedure of converting olefins to alcohols the most difficult and least efficient step is the initial hydroformylation conversion of olefins to aldehydes. In the art cited above, such conversions have been accomplished, but only using catalysts which are difficult to recover and in some cases are extremely toxic.

U.S. Pat. Nos. 3,636,159 and 3,652,676 teach rhodium-containing catalysts bound to polymers. However, these materials contain carbonyl groups and are not shown to be useful for hydrogenation.

It would therefore be of great benefit to provide a catalyst which has high levels of activity for the conversion of olefins to aldehyde (hydroformylation or oxo reaction) which employs non-toxic material, is easily prepared, and readily recovered. In addition, lack of sensitivity to oxygen would be of great benefit.

It is therefore an object of the present invention to provide a method and catalyst for hydroformylation and hydrogenation reactions, said catalysts being recoverable and reuseable. Other objects will become apparent to those skilled in this art as the description proceeds.

It has now been discovered according to the present invention that a catalyst having the general structure 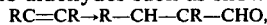 —M Cl$_3$ M is rhodium or iridium and ⓟ is a heterocyclic nitrogen-containing polymer has been found to be an effective heterogeneous hydroformylation and hydrogenation catalyst at temperatures of from about 60° to about 150° C. and hydrogen carbon monoxide gas pressures of from about 300 to 3500 psig for all classes of olefins producing an increased amount of linear normal aldehydes. When the reactor gas is altered to hydrogen, the catalyst further converts unsaturated organic materials to fully saturated materials under the same reaction conditions. The catalyst is oxygen stable, heterogeneous, and easily recovered.

Higher reaction temperatures are possible as the pressure exceeds about 2500 psig. Pressures can range up to about 3500 psig limited usually only by reactor material considerations. High temperatures without sufficient pressure will generally deactivate the catalyst.

Hydroformylation reactions are carried out in the presence of mixtures of hydrogen and carbon monoxide. This reaction requires 1 mole of carbon monoxide be present for each mole of olefin reactant. Therefore the most preferred ratio is about 1:1 H/CO respectively. Normally, the ratio of hydrogen to carbon monoxide will range from about 1:100 to 100:1 respectively, although from about 80:20 to about 20:80 respectively is preferred, and from about 60:40 to about 50:50 respectively is more preferred and 50:50 is most preferred.

The catalysts of the instant invention use a heterocyclic nitrogen-containing polymer as a combination polymer support and ligand for bound rhodium and iridium trihalide catalysts such as those having the formula MX$_3$ or hydrated form such as MX$_3$.AH$_2$O wherein X is selected from the group consisting of fluorine, chlorine, bromine, or iodine, A is the number of bound water molecules and M is rhodium or iridium. The catalysts of the invention are effective when non-polymer bound, but are not recoverable and are not as active as the polymer-bound catalyst.

The preparation of the instant catalyst is simple and chemically binds the catalyst to a polymer for easy recovery and reuse. Concisely, the rhodium or iridium trihalide material of choice is dissolved in a suitable organic solvent, the polymer is added (preferably polyvinylpyridine/divinylbenzene copolymer), the mixture is refluxed for a sufficient period of time to bind the metal halide to the polymer and the catalyst is purified by extraction. At the conclusion of the preparation, the catalyst and the rhodium complex are chemically bound, oxygen stable, and can be easily handled.

The prior art discloses many cases of amines being used as ligands in homogeneous hydrogenation and hydroformylation reactions. However, such soluble catalysts presents severe rhodium recovery problem, making them economically unsuitable for commercial applications. Some examples of descriptions of soluble catalysts can be found at Jurewicz et al, *Advanced Chemical Series*, 132, 240 (1974); Ogata et al, *Tokyo Kogyo Shikensho Hokoku*, 67, 340 (1972); Fell et al, *Chem.-Ing.-Tech.* 44, 708 (1972); and Abley et al, *Journal of Chemical Society*, C, 804 (1971). The present invention overcomes these limitations by chemically bonding the rhodium and iridium to an insoluble polymeric pyridine support, allowing recovery from the reaction mixture by direct filtration.

In distinct contrast to most rhodium containing hydroformylation catalysts, the catalyst of the invention do not require dry inert atmosphere of nitrogen, argon, helium, neon, or the like. The recovery and handling as well as synthesis can be carried out in a normal ambient environment while retaining catalyst activity. Excessive oxygen, exposure will tend to shorten catalyst life, and should be avoided; however, the catalyst will be effective for hydroformylation often exposure to oxygen.

The heterocyclic nitrogen-containing polymer to which the metal is bound may require a swelling solvent for good catalyst activity depending on the amount of cross-linking the polymer contains. Highly cross-linked polymers (above about 20–25%) will not need a swelling solvent. The polymer described is 1% crosslinked and does require a swelling solvent. The polymer bound catalysts of the present invention are extremely well suited for continuous fixed-bed reactions. However, use of the solvent would not affect the efficiency of the reaction and what may well be desirable in some processes because of handling consideration. However, it is emphasized that a solvent is not critical to the instant invention. Representative examples of suitable solvents useful for the instant invention are tetrahydrofuran, benzene, toluene, xylene, acetophenone, and dimethylformamide.

Representative examples of heterocyclic nitrogen containing polymers useful in the instant invention are polyvinylpyridint/divinylbenzene copolymers such as 4-vinylpyridine/divinylbenzene, 3-vinylpyridine/divinylbenzene, 2-vinylpyridine/divinylbenzene; also polyphenylquinoxaline/divinylbenzene copolymer, poly[N-vinylcarbazole]/divinylbenzene copolymer and polyvinylimidazole/divinylbenzene copolymer.

The invention is more concretely described with reference to the examples below wherein all parts and percentages are by weight unless otherwise specified. The examples are provided to exemplify the instant invention and not to limit it.

All olefins used in hydroformylation reactions in the examples below were percolated through a 30 centimeter×2 centimeter silica gel column prior to use. The examples illustrate the hydroformylation of both primary and internal olefins as well as hydrogenation efficiency for a variety of materials.

EXAMPLE 1

A 1% divinylbenzene 4-vinylpyridine copolymer (99% 4-vinylbenzene) in the amount of 14 grams was refluxed with 3 grams of rhodium trichloride.3H$_2$O in 200 ml of absolute ethanol and 40 ml of anhydrous tetrahydrofuran (THF) for 2 hours. The treated polymer was filtered and extracted with absolute ethanol for 24 hours then filtered and dried at 50° C. under vacuum for 8 hours. An ochre-colored product (16.9 grams) was collected. Elemental analysis of the catalyst indicated a composition of 4.23% hydrogen, 5.85% nitrogen, 6.5% chlorine, and 5% rhodium. The catalyst was then used in subsequent reactions.

EXAMPLE 2

A catalyst prepared as described in Example 1 (1 gram) was charged into an autoclave with 35 grams of benzene. The autoclave was fitted with the magnetic stirring bar to mix the catalyst and substrate during the reaction. The reactor was purged 3 times to 400 psig hydrogen prior to heating to reaction temperature. The reactor was quickly heated to 120° C. at which temperature the hydrogen gas pressure was adjusted to 900 psig. After 18.4 hours of reaction time, chemical analysis of the reaction mixture indicated a 55% net conversion of benzene to cyclohexane.

EXAMPLE 3

The catalyst was recovered from Example 2 by filtration of the reaction mixture and was subsequently charged with 20 ml of benzene (swelling solvent) into an autoclave. Thirty five grams of 1,7-octadiene was then added. The reactor was purged and the reaction carried out identically as described in Example 2 except that hydrogen gas pressure was maintained at 800 psig during the course of the reaction. After 0.33 hours of reaction time, chemical analysis of the reaction mixture indicated a 100% conversion of 1,7-octadiene to n-octane.

EXAMPLE 4

The catalyst was recovered and reswollen by the same method shown in Example 3. The olefin charged consisted of 35 grams of ethyl acrylate. The reaction was purged, heated and pressured with hydrogen to the same parameters described in Example 2. After 0.17 hours of reaction time chemical analysis of the reaction mixture indicated a 100% conversion of ethyl acrylate to ethyl propionate.

EXAMPLE 5

The catalyst was recovered from Example 4 by filtration and reswollen according to the method described in Example 2. The catalyst was then charged into an autoclave with 32 grams of allyl acetate. The reactor was purged, heated, and maintained under the same reaction conditions as described in Example 2. After 0.12 hours of reaction time, chemical analysis of the reaction mixture indicated a 100% conversion of allyl acetate to propyl acetate.

EXAMPLE 6

The catalyst was recovered from Example 5 and by filtration and reswollen according to the method discussed in Example 2. The reaction was carried out identically in all respects with Example 2 except that the olefin charged employed consisted of 32 g of 1-octene. After 2.25 hours of reaction time chemical analysis of the reaction mixture indicated a 100% conversion of 1-octene to n-octane.

EXAMPLE 7

The catalyst was recovered from Example 6 and by filtration and reswollen according to the method described in Example 2. An olefin charge consisting of 35 g of 7-tetradecene was added to the autoclave with the catalyst and the reactor purged 3 times to 900 psig with a gas mixture comprising 1:1 ratios of hydrogen and carbon monoxide. The reactor was then heated quickly to 120° C. and at this temperature the hydrogen carbon monoxide gas pressure was adjusted to 950 psig. After 8.15 hours of reaction time analysis by gas chromatograph (GC) of the reaction mixture indicated a 35% conversion of 7-tetradecene to $C_{15}$ aldehydes. The aldehyde product contained 12% n-pentadecanal.

EXAMPLE 8

The reactor containing reaction products of Example 7 was then purged 15 times to 900 psig with pure hydrogen, heated to 130° C. and at this temperature the hydrogen gas pressure was adjusted to 950 psig. After 3 hours of reaction time chemical analysis indicated a 100% conversion of the 7-tetradecene to n-tetradecane, and a 100% conversion of the $C_{15}$ aldehydes present at the start of the Example 7 reaction to $C_{15}$ alcohols.

EXAMPLE 9

The catalyst from the Example 8 reaction was recovered by filtration and reswollen as described in Example 2. The catalyst was placed in an autoclave together with 35 grams of 1-undecene and a reaction was carried out as described in Example 7 except that the reaction temperature was maintained at 130° C. After 9.53 hours of reaction time chemical analysis of the reaction mixture indicated a 15% conversion of 1-undecene to $C_{12}$ aldehydes. The $C_{12}$ aldehyde product contained a normal to branched ratio (n/i) of 2.88.

EXAMPLE 10

In order to quantify metal elution from the polymer catalyst, the products from the above reactions were sampled and analyzed for rhodium content. These findings together with a summary of each reaction are presented in Table 1.

Table I

| Example No. | Reactant | Product | % Conversion/ Reaction Time (Hr) | Reactor Gas | °C./ Psig | Rhodium Elution PPM |
|---|---|---|---|---|---|---|
| 2 | Benzene | Cyclohexane | 55/18.416 | $H_2$ | 120/900 | <0.4 |
| 3 | 1,7-Octadiene | n-octane | 100/0.33 | $H_2$ | 120/900 | 0.37 |
| 4 | Ethyl acrylate | Ethyl propionate | 100/0.166 | $H_2$ | 120/900 | <0.13 |
| 5 | Allyl acetate | Propyl acetate | 100/0.116 | $H_2$ | 120/900 | <0.20 |
| 6 | 1-Octene | n-octane | 100/2.25 | $H_2$ | 120/900 | <0.29 |
| 7 | 7-tetradecene | $C_{15}$ aldehydes | 35/8.15 (1:1) | $H_2/CO$ | 120/950 | 0.80 |
| 8 | Example 7 product | n-tetradecane and $C_{15}$ alcohols | 100/3.00 | $H_2$ | 130/950 | |
| 9 | 1-undecene | $C_{12}$ aldehydes | 15/9.53 (1:1) | $H_2/CO$ | 130/950 | 14.0 |

It should be noted that the catalyst was continuously recovered throughout the series of experiments and that surprisingly high yields were obtained in the last experiment in spite of the losses normally encountered during handling and reaction, indicating the efficiency of the instant invention.

EXAMPLE 11

Hydrated iridium trichloride (3 grams) is dissolved in 200 ml of absolute ethanol. 14 grams of a 1% divinylbenzene/4-vinylpyridine copolymer suspended in 40 ml of anhydrous THF are added and the mixture is refluxed for a period of time sufficient for the catalyst complex to form. The treated polymer is filtered, extracted with ethanol for a sufficient period of time to remove any unbound $IrCl_3$, and is dried in vacuum for 10 hours. The catalyst thus obtained is then used identically as described in Examples 2 through 9.

All olefinic bonds will react to some extent using the catalysts of the instant invention. Most useful olefins will contain up to about 25 carbon atoms and be in a liquid state at reaction conditions. The aldehydes of the instant invention are derived directly from the olefins used. Internal olefinic bonds can thus be isomerized to primary aldehydes.

While certain embodiments and details have been shown for the purpose of illustrating this invention, it will be apparent to those skilled in this art that various changes and modifications may be made herein without departing from the spirit or scope of the invention.

I claim:

1. A method for converting olefins to aldehydes comprising converting said olefins at temperatures of from about 60° C. to about 100° C. and pressures of from about 300 to about 3500 psig H/CO gas in the presence of a catalyst containing rhodium and iridium, wherein the catalyst is prepared by dissolving a rhodium or iridium trihalide compound having the general formula $MHX_3$, wherein M is rhodium or iridium, X is selected from the group consisting of florine, chlorine, bromine, or iodine, in an organic solvent, adding a polyvinylpyridine/divinylbenzene copolymer and refluxing the solution for a sufficient period of time to allow reaction to occur and purifying the catalyst by extraction.

2. A method as described in claim 1 wherein the organic solvent is selected from the group consisting of tetrahydrofuran, benzene, toluene, xylene, acetophenone and dimethylformamide.

* * * * *